United States Patent [19]

Grech et al.

[11] Patent Number: 5,518,692
[45] Date of Patent: May 21, 1996

[54] METHYL IODIDE AS A SOIL FUMIGANT

[75] Inventors: Nigel M. Grech; Howard D. Ohr; James J. Sims, all of Riverside, Calif.

[73] Assignee: The Regents of the University of California, Oakland, Calif.

[21] Appl. No.: 483,410

[22] Filed: Jun. 7, 1995

Related U.S. Application Data

[63] Continuation-in-part of Ser. No. 326,632, Oct. 20, 1994, abandoned.

[51] Int. Cl.$^6$ .................................................. B01J 19/00
[52] U.S. Cl. ...................... 422/37; 43/125; 47/DIG. 10; 422/1; 422/32; 422/40; 424/405
[58] Field of Search ...................................... 422/1, 28, 32, 422/37, 40; 47/DIG. 10; 43/125; 424/405, 667; 514/743

[56] References Cited

U.S. PATENT DOCUMENTS

| | | | |
|---|---|---|---|
| 2,403,435 | 1/1943 | Hammer | 167/39 |
| 2,407,333 | 10/1943 | Wenck et al. | 167/39 |
| 2,543,580 | 12/1946 | Kay | 167/39 |
| 2,794,727 | 6/1957 | Barrons | 71/2.7 |
| 2,875,118 | 2/1959 | Turner | 167/22 |
| 2,895,872 | 7/1959 | Meuli | 167/39 |
| 3,511,638 | 5/1970 | Joo et al. | 71/109 |
| 3,876,761 | 4/1975 | Shepherd | 424/78 |
| 3,979,179 | 9/1976 | Teng | 21/60.5 |
| 5,202,047 | 4/1993 | Corby | 252/106 |

OTHER PUBLICATIONS

USDA Workshop on Alternatives for Methyl Bromide 6/29–7/93 Doubletree Hotel, Crystal City, VA. U.S. Dept of Agriculture.
The Biologic and Economic Assessment of Methyl Bromide (NAPIAP) National Agricultural Pesticide Impact Assessment Program, U.S. Dept. of Agriculture.
Methyl Bromide Alternatives Conference, United Nations Environment Programme, Nov. 1992.
Yagi, K. et al., PNAS USA 90:8420–6423 (1993).
Rolston and Glauz, *Pesticide Science* 13:653 1982).
Price, N. R., *J. Stored Prod. Res.* 21(4):157–164 (1985).
Lindgren, D. L., *J. Economic Entomol.* 31:320 (1938).
Lindgren, D. L., *J. Economic Entomol.* 47:923–926 (1954).
Lehman, R. S., *J. Economic Entomol.* 47:659–661 (1942).
Rajendran, S. & Muthu, M., *Indian J. Ent.* 49 (3):363–369 (1987).
Hassall, K. A., *Ann. Appl. Biol.* 43:615–629 (1955).
Lovelock, J. E. et al., *Nature* 241:194–196 (1973).
Chameides, W. L. et al., *J. Geophys. Res.* 84(12):7383–73998 (1980).
Rassmussen, R. A. et al., *J. Geophys. Res.* 87(C4):3086–3090 (1982).
Korzh, V. D., *Atmospheric Environ.* 18(12):2707–2710 (1984).
Jeffers and Martin *Plant Disease* 70:1038–1043 (1986).
Ko & Hora, *Phytopathology* 61:707–710 (1971).

*Primary Examiner*—Robert J. Warden
*Assistant Examiner*—Krisanne M. Thornton
*Attorney, Agent, or Firm*—Robbins, Berliner & Carson

[57] ABSTRACT

Methyl iodide is employed as a soil fumigant for the effective control of plant pathogens, nematodes, bacteria and weeds. Methyl iodide is employed in substantially the same manner as is customary for use of methyl bromide, and is at least as effective as methyl bromide when used in comparable amounts.

10 Claims, No Drawings

METHYL IODIDE AS A SOIL FUMIGANT

BACKGROUND OF THE INVENTION

This application is a continuation-in-part of Ser. No. 08/326,632 filed Oct. 20, 1994 now abandoned.

The present invention relates generally to the fields of biology and agriculture. More particularly, the present invention relates to compositions and methods for use in fumigation of soils.

The control of plant pathogens, nematodes and weeds is of central importance to the agriculture industry. In particular, the substantial reduction or complete elimination of nematode populations in soils is critical to initial plant growth, productivity and life-span. Pathogenic fungi and nematodes develop on the extensive root systems of both annual and perennial crops, damaging them severely. Moreover, they persist in the soil after crop removal and need to be eliminated before replanting of new crops. Among the fungi and nematodes of particular significance to agriculture are the following: root rot pathogens (Phytophthora spp., Pythium spp., Rhizoctonia spp., Fusarium spp.); vascular wilt pathogens (Verticillium spp., Fusadum spp.); root knot nematodes (Meloidogyne spp.); root lesion nematodes (*Pratylenchus vulnus*); ring nematodes (*Circonemella xenoplax*); stubby root nematodes (Paratdchodorus spp.); stem and bulb nematodes (*Dilylenchus dipsaci*); cyst nematode (*Heterodera schachtii*); citrus nematode (*Tylenchulus semipenetrans*) and the burrowing nematode (*Radopholus similus*).

To date, the only approaches which have been used successfully to combat plant pathogens and nematodes have been crop rotation or fallowing for at least four years, use of pathogen and nematode-resistant crops and soil fumigation. Rotation has limited value for control in many cases, because of the wide host range of many species of fungi and nematodes; moreover, many of the non-host crops provide only a low per acre return. Resistance to plant pathogens and nematodes is available only in a few crops, and resistant cultivars may not be developed in the foreseeable future for many crops of significant commercial interest. Therefore, soil fumigation remains the best alternative for control of plant pathogens and nematodes.

Methyl bromide ($CH_3Br$) is extremely important to United States agriculture [U.S.D.A. *The Biological and Economic Assessment of Methyl Bromide*, U.S.D.A. Publication (1993)]. It is the most widely used and most effective universal fumigant in the world. It is used extensively for soil fumigation, as a commodity quarantine treatment (export and imports) to control a variety of pests on numerous crops, and as a structural fumigant for wood destroying pests.

According to the Montreal protocol of 1991 (as amended in 1992), methyl bromide (MBr) was categorized as an ozone depleting chemical with an ozone depleting potential (ODP) of greater than 0.2 compared to trichlorofluoromethane (cfc 11), a refrigerant used as a reference gas having an ODP of 1. Title Five of the Clean Air Act (Stratospheric Ozone Protection), which was added in the 1990 amendments thereto, indicates in Section 602 that the U.S. Environmental Protection Agency (EPA) must list as a Class 1 ozone depleter any substance with an ODP of 0.2 or greater. Once designated, all production must be phased out by the year 2000. MBr has an ODP of 0.7; 30–40% of total ozone depletion is said to be as a result of bromine radicals, which are 30–60 times more efficient ozone depleters than chlorine [Pyle, J. A. et al., In: *Scientific Assessment of Ozone Depletion*, eds. Albritton, D. L. et al., World Meteorol. Org., Geneva (1991), pp. 6.1–6.19].

Evidence on the loss of MBr to the atmosphere after soil fumigation indicates that of the total amount applied to the soil for fumigation, approximately 87% is lost to the atmosphere within seven days [Yagi, K. et al., *PNAS USA* 90: 8420–8423 (1993)]. On reaching the stratosphere MBr undergoes photo-oxidation, releasing bromine atoms which enter the ozone depletion cycle. MBr loss from fumigated soils is further supported by studies which indicated a loss of as much as 70% of the applied MBr to the atmosphere through the tarp and after the tarp is removed [Rolston and Glauz, *Pesticide Science* 13: 653 (1982)].

In 1990, approximately 64,000,000 pounds of MBr were used in the U.S., of which 44–49 million pounds were used for soil fumigation (control of insects, nematodes, weeds, plant pathogenic microbes and vertebrate and invertebrate pests), 5 million for post harvest and quarantine treatments, 4–9 million pounds for fumigating structures and 6 million pounds for use as chemical intermediates. Thus, approximately 80% of the total is used for agriculturally related purposes.

As currently available alternatives to MBr are less effective and/or more expensive, the removal of MBr will be very costly. Annual losses to U.S. producers and consumers is estimated to be in the region of 1.5 billion dollars. This figure does not account for the losses due to post harvest and quarantine losses as well as structural fumigation losses. California and Florida are the largest users of MBr (approximately 25,000,000 pounds combined) in the U.S., and hence will be most heavily affected by its removal. MBr removal would most adversely affect such commodities as tomatoes, strawberries, peppers, melons and ornamentals. The loss of MBr would thus be extremely costly to both agricultural producers and consumers as well as having a substantial impact on the U.S. economy. Nonetheless, it is the general consensus of those working in the field that no approach is currently available that will achieve the same level of broad-spectrum pest management as methyl bromide; chemical and nonchemical approaches that are available can provide some level of agricultural pest management, but generally with narrower activity and lower crop yields and quality. Therefore, there is clearly a need for alternatives to MBr.

It is an object of the present invention to provide methods and compositions for use in soil fumigation which ameliorate at least some of the problems attendant to prior art methods.

SUMMARY OF THE INVENTION

In accordance with the present invention, methyl iodide is employed as a soil fumigant for the effective control of plant pathogens, nematodes, bacteria and weeds. Methyl iodide may be employed in substantially the same manner as is customary for use of methyl bromide, and is at least as effective as methyl bromide when used in comparable amounts.

DETAILED DESCRIPTION OF THE INVENTION

While the present invention is not bound to any particular theory, methyl iodide appears to be totally analogous to methyl bromide in its ability to act as a biocide. The generally accepted mechanism explaining the activity of a member of the lower alkyl halide series is that it reacts via bimolecular nucleophilic displacement ($S_N2$) reaction with functional groups such as $NH_2$ and SH in various amino acids and peptides in target organisms [Price, N. R., *J. Stored Prod. Res.* 21(4): 157–164 (1985)]. Methyl iodide reacts at approximately the same rate as methyl bromide under most $S_N2$ conditions that have been reported.

There have been several reports in the literature of the use of methyl iodide as a fumigant for control of insect populations in stored grain [Lindgren, D. L., *J. Economic Entomol.* 31: 320 (1938); Lindgren, D. L. et al., *J. Economic Entomol.* 47: 923–926 (1954); Lehman, R. S., *J. Economic Entomol.* 35: 659–661 (1942); Rajendran, S. & Muthu, M., *Indian J. Ent.* 49(3): 363–369 (1987); Hassail, K. A., Ann. Appl. Biol. 43: 6 15–629 (1955)]. Nonetheless, it would simply not have been possible to predict that an agent having utility in control of insect populations in stored grain would in fact have any utility whatsoever in fumigation of soils for elimination of plant pathogens, nematodes, bacteria and/or weeds.

Soil can modify the chemical activity of fumigants. Whereas activity of an agent may be high in air, it may have much less activity in soil [Lehman, R. S., *J. Economic Entomology,* 35: 659–661 (1942)]. Indeed, fumigation of stored grain and its expectations are relatively simple when compared to the complexity of fumigating soils and the expectations from such fumigations. Humidity in stored grain is uniform throughout the product, whereas in soil it can vary greatly. In addition, particle size in stored grain is fairly uniform, as are the airspaces between particles; this makes fumigation of grain relatively simple. In soil, the particle sizes and airspaces vary widely, substantially complicating fumigation.

Further, the target organisms in stored grain are fairly limited in variety and quite different from the large variety and number of target organisms in the soil. Fumigation in stored grain targets insects; fungi, nematodes and bacteria are not usually a problem when the humidity is kept low, and weeds would not be affected by a fumigation that did not also kill the grain. In soil, fumigation is expected to kill fungi, nematodes, weed seeds, insects, and vertebrate and invertebrate pests.

As a consequence, many fumigants used for stored products are generally not used as soil fumigants. For example, phosphine is currently registered and used for stored products but not used in soil where it is apparently ineffective. Some pests are resistant to phosphine, and it is not effective under 50° F.; moreover, it requires a fumigation time of 3–5 days and is highly flammable. Similarly, esters of formate (e.g., methyl formate) are effective in treating stored products, but are much less effective in soil. Therefore, it is clear that compositions useful as stored products fumigants are not necessarily useful as soil fumigants.

In trials carried out in accordance with the invention, methyl iodide has proven to be an effective chemical for the fumigation of five species of soil borne plant pathogenic fungi, one saprophytic fungus, three weeds and two nematodes. In the majority of trials in both the laboratory and the field, MI Was effective at rates that were equivalent to 0.5 to 1.0 lb of methyl bromide per 100 ft³. In only one trial, on one fungus, for unknown reasons MI did not eliminate the fungus at any rate (Table 3); however, this fungus was eliminated in a different trial (Table 2). In direct comparison field trials MI was as effective as MBr (Tables 7 and 8) in eliminating the pathogen. In three laboratory trials, MI was more effective as a soil fumigant than seven other alkyl iodides. Therefore, methyl iodide is at least as effective as methyl bromide in fumigating soil to eliminate soil borne plant pathogenic fungi.

Methyl iodide absorbs UV radiation most strongly in the UVC range (100 to 280 nm) with a maximum approximating 260 nm, although strong absorption occurs at longer (UVB) wavelengths (280 to 315 nm). It is these which are believed to be responsible for tropospheric degradation. UV absorption causes photodegradation, leading to the formation of methyl radicals and iodine radicals.

The estimated lifetime of methyl iodide in the troposphere is between about 50 hours and about 8 days, as compared to methyl bromide with an estimated atmospheric lifetime of 1.5 years [Lovelock, J. E. et al., *Nature* 241.: 194–196 (1973); Chameides, W. L. et al., *J. Geophys. Res.* 85(12): 7383–7398 (1980)]. As a consequence, MI has not been intimated in stratospheric ozone depletion [Rassmussen, R. A. et al., *J. Geophys. Res.* 87(C4): 3086–3090 (1982)]. MI has a vapor pressure of approximately 25% that of MBr and hence is less volatile, and has a similar solubility in water. Due to its rapid photolysis in the troposphere, MI (unlike MBr) is rapidly removed from the atmosphere. MI occurs at saturated levels in the ocean and is principally produced by marine algae [Chameides et al. (1990), supra; Korzh, V. D., *Atmospheric Environ.* 18(12): 2707–2710 (1984)]; it is postulated that this is the principal source of MI in the marine boundary layer. Levels of MI in the atmosphere adjacent to the marine boundary layer are usually 2.5 times lower [Korzh (1984), supra].

As with other halogens, the postulated chemistry of iodine if it reached the stratosphere suggests that it would be very effective in ozone destruction [Rolston & Glauz (1982), supra]. However, the above reasons and the very short life of MI in the atmosphere negate the likelihood of any substantial migration of MI to the stratosphere. As the atmospheric life of MBr is approximately 1.5 years, it clearly has an ozone-depleting potential several orders of magnitude higher than MI. Studies on trifluoromethyl iodide have not shown any involvement of this substance with ozone depletion. This substance is similarly broken down by solar radiation to reactive radicals; as with $CH_3I$, it does not reach the stratosphere due in part to its short tropospheric half life.

Application of MI in accordance with the present invention may be effected by a number of different procedures as are currently routinely employed for soil treatments with MBr. Thus, for example, MI may be applied to the soil by tractor mounted injectors on tynes, manually in canisters and via an existing irrigation system or as a gas through lay flat tubing. MI may advantageously be pre-heated by passage through a heat exchanger prior to delivery; pre-heating vaporizes MI for more rapid and even distribution and increases its activity. In addition, MI may be dissolved in suitable solvents (e.g., lower alcohols, acetone, mixtures of water with acetone or alcohol, etc.) to assist in dispersion of the material in the soil. Further, it is contemplated as within the scope of the invention to apply mixtures of MI with other fumigants (e.g., carbon disulfide or chloropicrin) in ratios comparable to those currently employed with MBr. For example, a mixture of 67% MI and 33% chloropicrin would be effective, as would a mixture of about 98% MI with 2% chloropicrin as a warning agent. In general, it is preferred that tarping be undertaken immediately following fumigation. The duration of the fumigation treatment and the application and removal of tarps should be consistent with contemporary practice in connection with MBr treatments.

A wide range of application rates of MI have been found suitable in accordance with the present invention. Those working in the field would of course be readily able to determine in an empirical manner the optimum rates of application for any given combination of crops, soils and plant pathogens. In general, application of MI is preferably effected at a rate of about 2 lb/acre to about 2000 lb/acre (2.23 kg/hectare to about 2250 kg/hectare), more preferably about 500 lb/acre to about 1500 lb/acre (560 kg/hectare to about 1680 kg/hectare), and most preferably about 600 lb/acre to about 1200 lb/acre (670 kg/hectare to about 1340 kg/hectare). Applications of MI at rates substantially in excess of about 2000 lb/acre (2250 kg/hectare) would not be expected to provide any significant advantage over applications within the preferred ranges specified herein, but are nonetheless regarded as well within the scope of the present invention.

Soil fumigation with MI in accordance with the present invention has been found to be extremely effective in the substantial or complete elimination of a wide variety of plant pathogens. For purposes of the present invention, substantial elimination of a plant pathogen is intended to mean reduction in the population of the pathogen by about 90%, more preferably about 95%, and most preferably about 100%. In general, treatment in accordance with the present invention by application of an amount of MI within the preferred ranges specified herein results in almost complete elimination of plant pathogen populations within the present limits of customary means employed for the detection thereof.

Plant pathogenic organisms successfully controlled or eliminated by treatments in accordance with the present invention include, but are not limited to, nematodes, fungi and weeds. Particular plant pathogens and nematodes controlled or eliminated by application of MI include, but are not limited to, the following: root rot pathogens (Phytophthora spp., Pythium spp., Rhizoctonia spp., Fusarium spp.); vascular wilt pathogens (Verticillium spp., Fusarium spp.); root knot nematodes (Meloidogyne spp.); root lesion nematodes (*Pratylenchus vulnus*); ring nematodes (*Circonemella xenoplax*); stubby root nematodes (Paratrichodonts spp.); stem and bulb nematodes (*Ditylenchus dipsaci*); cyst nematode (*Heterodera schachtii*); citrus nematode (*Tylenchulus semipenetrans*) and the burrowing nematode (*Radopholus similus*). While the definition of "weed" in agriculture is of course purely contextual, among the types of plants generally sought to be controlled or eliminated the following should be mentioned: cheeseweed (Malva spp.), field bindweed (*Convolvuhts arvensis*), annual bluegrass (*Poa annua*), etc. MI treatment is also useful in the control of other pathogens, such as crown gall (*Agrobacterium tumefaciens*) and other plant pathogenic bacteria. Finally, as previously reported in the literature treatment with MI may also reduce or eliminate the populations of a variety of insects. Insects of particular interest in agriculture which are controlled or eliminated during a treatment in accordance with the present invention include, but are not limited to, the following: fungal gnat larvae, soil mealy bugs, phylloxera, ants, termites and animal parasites, etc.

The invention may be better understood with reference to the accompanying examples, which are intended for purposes of illustration only and should not be construed as in any sense limiting the scope of the invention as defined in the claims appended hereto.

Examples

Fungi used were maintained as stock cultures and transferred to 15 cm potato dextrose agar (PDA) petri plates as needed. Plate colonies were allowed to grow at ambient laboratory temperature (ca. 25° C.). When ¾ of the agar surface was covered the cultures were considered ready for use. Circular plugs, 18 mm in diameter, were cut from the leading edge of colony growth with a sterile cork borer and used to inoculate sterile millet seed.

Three hundred ml of white millet seed was placed in 950 ml (1 qt) Mason canning jars, rinsed with distilled water and drained. The jars were sealed with canning lids and rings. The lids had 12 mm holes plugged by nonabsorbent cotton. The jar tops were then covered with a double layer of heavy brown paper secured by masking tape. The jars were placed in a deep, autoclavable plastic pan to which water was added until it passed the level of seed in the jars. The seed was sterilized for 30 min at 250° C. and 1 atm of pressure. After sterilizing, the seed was cooled to room temperature and 100 ml of a 1:9 sterile V-8 juice-water mixture was added to each jar. The millet was then inoculated with 10 circular agar plugs of the appropriate fungus and incubated at laboratory temperatures until used or discarded. Jars were shaken periodically to distribute the fungal growth. Seed not used within 30 days was discarded. For smaller amounts of inoculum, 100 ml of seed was used and incubated in 500 ml Erlenmeyer flasks. These flasks were sealed with a cotton plug and covered with aluminum squares.

When used, millet seed cultures were removed from the jars, broken up by hand into individual seeds and added to the appropriate soil for the experiment. The seed culture was thoroughly mixed into the soil at a ratio of 300 ml to 3.5 l of soil.

Soils used for inoculum were a 1:1 potting mix of topsoil and sawdust or wood shavings for the laboratory experiments and field soil sieved through a No. 10 screen for field trials. Moisture in the inoculum soil ranged from 8.4% to 32%, depending on the trial. Soils were sterilized by autoclave before adding inoculum.

Inoculum containers were made from 45 ml clear plastic vials (No. 55-12, Thornton Plastic Co., Salt Lake City, Utah). Each vial was perforated by sixteen 1 cm holes using an Unger electric soldering iron with ½ cm tip. The holes were distributed in two rows of 4 and two of three (on opposite sides) with one hole in the bottom and one in the white plastic snap cap.

After the vials were filled with inoculum, those used in laboratory trials were placed on a 1 cm layer of potting mix in 1893 ml (2 qt) Mason canning jars and covered with the same soil to a depth of 1 to 1½ cm. The jars were placed under a fume hood and a measured amount of the fumigant was injected into each jar using a micropipette with the appropriate tip. The fumigant was placed on the soil just inside the mouth of the jar. The jars were sealed immediately with a solid canning lid and ring and placed horizontally on the laboratory bench to incubate. Incubation was for 1, 2 or 3 days depending on the trial. Each experiment contained 4 replications of 25 seeds each per treatment.

After fumigation the vials were removed from the soil and ventilated under the hood for one hour. After ventilating the seed were separated from the soil by sieving through a No. 10 soil sieve. Twenty five seeds from each replicate were chosen and placed on agar in 15 cm petri plates. For Pythium spp. PARP medium was used, and for Phytophthora PARPH medium [Jeffers & Martin, *Plant Disease* 70: 1038–1043 (1986)]; for Rhizoctonia, a medium was used as reported in the literature [Ko & Hora, *Phytopathology* 61: 707–710 (1971)]. Other fungi were plated on ¼ strength PDA medium [Plant Pathologists Pocketbook (1968) Commonwealth Mycological Institute, p. 239]. After plating seeds were incubated at laboratory temperatures and surveyed for growth after 2 days. Seeds showing growth were counted and the plates checked until no more growth appeared, usually 3–4 days. After the results were recorded the plates were disposed of by sterilization.

In field trials the inoculum was prepared as described above and placed at depths of 2.5, 15 and 30 cm half way between the center and one corner of each plot. The plots were 3×3 m and the corner for placement of the inoculum was chosen randomly. Field trials were block randomized with 4 replications per treatment. After the fumigant was applied the plots were covered with 4 mil clear polyethylene plastic sheeting with the edges buried 7 cm.

Methyl bromide was prepared by storing 454 g containers and laboratory glass beakers 14 h in a portable ice chest with frozen $CO_2$. When used, the treatment amount was measured, poured into a chilled beaker, placed on the soil surface in the center of the plot, and covered with an inverted 15 cm black plastic plant pot. Methyl iodide was treated the same way but was not prechilled. The plot was then covered with plastic sheet. The control was no treatment covered with plastic. After 4 days the plastic was removed and the plots were allowed to aerate for 2 days. The inoculum vials were then removed and evaluated as described.

All fumigation concentrations were based on a methyl bromide application rate of 0.454 kg/2.8 $m^3$ (1 lb/100 $ft^3$), equal to 4.78 moles/2.8 $m^3$ for field trials and 1.69 µM/ml for laboratory trials.

EXAMPLE 1

This series of trials utilized *Phytophthora cinnamomi* and *Rhizoctonia solanis* as the test organisms. MI concentrations used were 1.69, 1.27, 0.84 and 0.42 µM/ml. Fumigation time periods were 24, 48 and 72 hours.

In this series all non-treated controls for both Phytophthora and Rhizoctonia had a 100% recovery rate based on an average of 4 replications of 25 seeds each. Cultures of Phytophthonia and Rhizoctonia fumigated 1 day at 0.42 µM/ml had recovery rates of 19% and 72%, respectively. After 2 days both had no recovery, while after 3 days at this concentration Rhizoctonia had a 1% recovery rate. All other concentrations were completely effective with no recovery of either fungus.

EXAMPLE 2

This series of trials utilized *P. cinnamomi*, *R. solani* and *P. citrophthora* as the test organisms. MI concentrations were 1.69, 1.27, 0.84, 0.42 and 0.21 µM/ml. Fumigation time periods were 24, 48 and 72 hours.

Upon collecting data it was found that the Rhizoctonia culture was contaminated with an Aspergillus sp. so data was collected on that species. All non-treated controls for all three organisms for all three time periods were 100% viable. The lowest concentration of 0.21 µM/ml MI (=0.125 lb MBr/100 $ft^2$) was ineffective for all three time periods for *P. citricola* and the 1 day and 2 day periods for *P. cinnamomi* and Aspergillus sp. with 100% recovery. At 3 days at this concentration both *P. cinnamomi* and Aspergillus had a recovery rate of 55%. At 0.42 µM/ml MI (=0.250 lb MBr/100 $ft^2$) *P. citricola* had a 54% recovery after 1 day and 0 after 2 and 3 days, while *P. cinnamomi* had 65% at 1 day and 0 at 2 and 3 days; Aspergillus had 25% at 1 day and 0 after 2 and 3 days. At 0.84 µM/ml MI (=0.5 lb MBr/100 $ft^2$) there was no recovery of *P. citricola*, while *P. cinnamomi* had a 25% recovery after 2 days but 0 for day 1 and 3; Aspergillus had a 20% recovery after 1 day but 0 for days 2 and 3. Concentrations of MI at 1.27 µM/ml (=0.75 lb MBr/100 $ft^2$) and 1.69 µM/ml (=1.0 lb MBr/100 $ft^2$) for all time periods had 0 recovery (Table 1).

In all of the tables, numbers followed by different letters are significantly different at p=0.05 using the Duncan-Waller T test.

TABLE 1

| µM/ml MI | Days | Recovery % | Note |
|---|---|---|---|
| *P. citricola* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 100 | a |
| 0.42 | 1 | 54 | bc |
| 0.42 | 2 | 0 | d |
| 0.42 | 3 | 0 | d |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |

| ml MI | Days | Recovery % | Note |
|---|---|---|---|
| *P. cinnamomi* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.42 | 1 | 65 | b |
| 0.21 | 3 | 55 | bc |
| 0.84 | 2 | 25 | cd |
| 0.42 | 2 | 0 | d |
| 0.42 | 3 | 0 | d |
| 0.84 | 1 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| Aspergillus | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 55 | bc |
| 0.42 | 1 | 25 | cd |
| 0.84 | 1 | 20 | d |
| 0.42 | 2 | 0 | d |
| 0.42 | 3 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |

EXAMPLE 3

This series of trials utilized *P. cinnamomi*, *P. citricola*, *P. parasitica* and *R. solani*. MI concentrations were 1.69, 1.27, 0.84, 0.42, and 0.21 μM/ml. Fumigation time periods were 24, 48 and 72 h.

Control recovery for *P. cinnamomi* was 100 % at 1 day, 99% at 2 days and 100% at 3 days. The *P. cinnamomi* recovery rate at 0.21 μM/ml MI (=0.125 lb MBr/100 ft$^2$) was 62% after 1 day, 64% after 2 days and 62% after 3 days. At 0.42 μM/ml MI (=0.25 lb MBr/100 ft$^2$) the rate after 1 day was 39%, after 2 days 23% and after 3 days 5%. There was no recovery at the higher concentrations of MI at 0.84 μM/ml (=0.5 lb MBr/100 ft$^2$), 1.27 μM/ml (=0.75 lb MBr/100 ft$^2$) and 1.69 μM/ml (=1.0 lb MBr/100 ft$^2$) for any time period (Table 2).

For *P. citricola* recovery rates after 1 day were control 100%, 0.21 μM/ml MI 100%, 0.42 μM/ml MI 100%, 0.84 μM/ml MI and higher 0%. After day 2 the control was 100%, 0.21 μM/ml MI was 85%, 0.42 μM/ml MI was 4% with all higher concentrations 0%. After 3 days the control was 99%, the 0.21 μM/ml MI was 61% and all other concentrations were 0 (Table 2).

For *P. parasitica* recovery for the control, 0.21 and 0.42 μM/ml MI after 1 day were all 100% and all higher concentrations were 0. After 2 days the control and 0.21 μM/ml MI recovery was 100%, and at 0.42/IM/ml MI it was 54%; all other concentrations were 0. After 3 days exposure recovery of the control was 98%, 0.21 μM/ml MI was 100% and 0.42 μM/ml MI was 76%; all other concentrations were 0 (Table 2).

For Rhizoctonia after 1 day recovery was 100% for the control, 0.21 and 0.42 μM/ml MI and 29% for 0.84 μM/ml MI. All other concentrations were 0. After 2 days the control and 0.21 μM/ml MI were 100 %, 0.42 was 93% and all other concentrations were 0. After 3 days the control and 0.21 μM/ml MI were recovered at 100% and 0.42 at 48%; all other concentrations were 0 (Table 2).

TABLE 2

| μM/ml MI | Days | Recovery % | Note |
|---|---|---|---|
| *P. citricola* | | | |
| 0 | 1 | 100 | a |
| 0 | 2 | 100 | a |
| 0 | 3 | 100 | a |
| 0.21 | 1 | 100 | a |
| 0.42 | 1 | 98 | a |
| 0.21 | 2 | 85 | ab |
| 0.21 | 3 | 61 | c |
| 0.42 | 2 | 4 | d |
| 0.42 | 3 | 0 | d |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| *P. cinnamomi* | | | |
| 0 | 1 | 100 | a |
| 0 | 2 | 100 | a |
| 0 | 3 | 100 | a |
| 0.21 | 2 | 72 | bc |
| 0.21 | 1 | 62 | c |
| 0.21 | 3 | 62 | c |
| 0.42 | 1 | 39 | c |
| 0.42 | 2 | 23 | d |
| 0.42 | 3 | 5 | d |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| *P. Parasitica* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 100 | a |
| 0.42 | 1 | 100 | a |
| 0.42 | 3 | 76 | ab |
| 0.42 | 2 | 54 | bc |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| *R. Solani* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 100 | a |
| 0.42 | 1 | 100 | a |
| 0.42 | 2 | 100 | a |
| 0.42 | 3 | 48 | bc |
| 0.84 | 1 | 29 | c |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |

EXAMPLE 4

These trials utilized *P. citrophthora, P. citricola, P. parasitica* and *R. solani*. MI concentrations were 1.69, 1.27, 0.84, 0.42, and 0.21 μM/ml. Fumigation time periods were 24, 48 and 72 hours.

After 1 day recovery of *P. citrophthora* was 100% for the control and 0.21 μM/ml MI. After 2 days control recovery was 100% and at 0.21 μM/ml MI it was 32%. After 3 days recovery was 100% for the control and 10% for 0.21 μM/ml MI. All other exposures were 0.

For *P. citricola* the control at 1 day exposure was recovered 100% and 0.21 μM/ml MI recovery was 33%. After 2 days recovery was 100% for the control, 1% for 0.21 μM/ml MI and 2% for both 0.84 and 1.69 μM/ml MI. After 3 days recovery for the control was 100%; recovery at all other exposures was 0.

For *P. parasitica* recovery in the control was 100% for all three time periods while at 0.21 μM/ml MI recovery at 1 day was 98% and at 2 days was 19%. All other exposures were 0.

In this trial recovery of Rhizoctonia was 100% for all three time periods for the control and 0.21 μM/ml MI and for 1 day of 0.42 μM/ml MI. Recovery at 2 days of 0.42 μM/ml MI was 32% and at 3 days was 91%. At 0.84 μM/ml MI recovery was 30%, 44% and 45% for 1, 2 and 3 days, respectively. At 1.27 μM/ml MI recovery was 17%, 43% and 68% for the same three time periods. At 1.69 μM/ml MI recovery was 20% at one day, 53% at 2 days and 78% at 3 days.

TABLE 3

| μM/ml MI | days | recovery % | note | μM/ml MI | days | recovery % | note |
|---|---|---|---|---|---|---|---|
| *P. citricola* | | | | | | *P. citrophthora* | |
| 0 | 1 | 100 | a | 0 | 1 | 100 | a |
| 0 | 2 | 100 | a | 0 | 2 | 100 | a |
| 0 | 3 | 100 | a | 0 | 3 | 100 | a |
| 0.21 | 1 | 33 | b | 0.21 | 1 | 100 | a |
| 1.69 | 2 | 2 | c | 0.21 | 2 | 10 | b |
| 0.21 | 2 | 1 | c | 0.21 | 3 | 10 | b |
| 0.21 | 3 | 0 | c | 0.42 | 1 | 0 | c |
| 0.42 | 1 | 0 | c | 0.42 | 2 | 0 | c |
| 0.42 | 2 | 0 | c | 0.42 | 3 | 0 | c |
| 0.42 | 3 | 0 | c | 0.84 | 1 | 0 | c |
| 0.84 | 1 | 0 | c | 0.84 | 2 | 0 | c |
| 0.84 | 2 | 0 | c | 0.84 | 3 | 0 | c |
| 0.84 | 3 | 0 | c | 1.27 | 1 | 0 | c |
| 1.27 | 1 | 0 | c | 1.27 | 2 | 0 | c |
| 1.27 | 2 | 0 | c | 1.27 | 3 | 0 | c |
| 1.27 | 3 | 0 | c | 1.69 | 1 | 0 | c |
| 1.69 | 1 | 0 | c | 1.69 | 2 | 0 | c |
| 1.69 | 3 | 0 | c | 1.69 | 3 | 0 | c |
| *P. parasitica* | | | | | | *R. solani* | |
| 0 | 1 | 100 | a | 0 | 1 | 100 | a |
| 0 | 2 | 100 | a | 0 | 2 | 100 | a |
| 0 | 3 | 100 | a | 0 | 3 | 100 | a |
| 0.21 | 1 | 98 | a | 0.21 | 1 | 100 | a |
| 0.21 | 2 | 19 | b | 0.21 | 2 | 10 | a |
| 0.21 | 3 | 0 | b | 0.21 | 3 | 100 | a |
| 0.42 | 1 | 0 | b | 0.42 | 1 | 100 | a |
| 0.42 | 2 | 0 | b | 0.42 | 3 | 91 | ab |
| 0.42 | 3 | 0 | b | 1.69 | 3 | 78 | abc |
| 0.84 | 1 | 0 | b | 1.27 | 3 | 68 | bcd |
| 0.84 | 2 | 0 | b | 1.69 | 2 | 53 | cde |
| 0.84 | 3 | 0 | b | 0.84 | 3 | 45 | def |
| 1.27 | 1 | 0 | b | 0.84 | 2 | 44 | def |
| 1.27 | 2 | 0 | b | 1.27 | 2 | 43 | def |
| 1.27 | 3 | 0 | b | 0.42 | 2 | 32 | ef |
| 1.69 | 1 | 0 | b | 0.84 | 1 | 30 | efg |
| 1.69 | 2 | 0 | b | 1.69 | 1 | 20 | fg |
| 1.69 | 3 | 0 | b | 1.27 | 1 | 17 | fg |

EXAMPLE 5

Alkyl iodides tested were methyl iodide, 1-iodoethane, 1-iodopropane, 2-iodopropane, 1.-iodobutane, 1-iodopentane, diiodomethane, and 1-iodo-2-methylpropane. Inoculum was prepared and trials were performed as in Example 1. The chemicals were compared on a molar basis with rates of 1.27 and 0.42 μM/ml (equal to ¾ lb and ¼ lb methyl bromide/100 ft$^3$, respectively). The test Organism was *Phytophthora parasitica*. Soil moisture was 24%. Fumigation exposure was 48 hours with 4 replications of 25 seeds each per treatment.

In this trial methyl iodide was the most effective compound with 0 recovery at both concentrations (1.27 and 0.42 μM/ml =to ¾ lb MBr and ¼ lb MBr/100 ft$^3$). This was followed by diiodomethane with a 62% recovery at the high concentration. All other concentrations were not significantly different from the control (Table 4).

TABLE 4

| Chemical | μM/ml MI | % survival | Note |
|---|---|---|---|
| None | 0 | 97 | a |
| 1-iodo-2-methyl-propane | 1.27 | 93 | a |
| 1-iodo-2-methyl-propane | 0.42 | 98 | a |
| 1-iodo-pentane | 1.27 | 92 | a |
| 1-iodo-pentane | 0.42 | 96 | a |
| 1-iodo-butane | 1.27 | 90 | a |
| 1-iodo-butane | 0.42 | 93 | a |
| 2-iodo-propane | 1.27 | 94 | a |
| 2-iodo-propane | 0.42 | 92 | a |
| 1-iodo-propane | 1.27 | 94 | a |
| 1-iodo-propane | 0.42 | 91 | a |
| 1-iodo-ethane | 1.27 | 81 | a |
| 1-iodo-ethane | 0.42 | 82 | a |
| Di-iodo-methane | 0.42 | 84 | a |
| Di-iodo-methane | 1.27 | 62 | b |
| Methyl iodide | 0.42 | 0 | c |
| Methyl iodide | 1.27 | 0 | c |

EXAMPLE 6

The soil was prepared for this trial as in Example 5; soil moisture was 32%. Rates used were 1.27 and 0.42 μM/ml for methyl iodide and 2.54 and 1.27 μM/ml for all other chemicals. Fumigation exposure was 48 hours with 4 replications of 25 seeds each per treatment. Methyl iodide was again the most effective compound with 0 recovery at both rates (1.27 and 0.42 μM/ml=to ¾ lb and ¼ lb/100 ft$^3$). This was followed by 1-iodoethane at 2.54 μM/ml (=to 1.5 lb MBr/100 ft$^3$). All other concentrations were not significantly different from the control.

TABLE 5

| Chemical | μM/ml MI | % survival | Note |
|---|---|---|---|
| None | 0 | 98 | a |
| 1-iodo-2-methyl-propane | 2.54 | 100 | a |
| 1-iodo-2-methyl-propane | 1.27 | 100 | a |
| 1-iodo-pentane | 2.54 | 100 | a |
| 1-iodo-pentane | 1.27 | 100 | a |
| 1-iodo-butane | 2.54 | 100 | a |
| 1-iodo-butane | 1.27 | 100 | a |
| 2-iodo-propane | 2.54 | 99 | a |
| 2-iodo-propane | 1.27 | 100 | a |
| 1-iodo-propane | 2.54 | 100 | a |
| 1-iodo-propane | 1.27 | 100 | a |
| Di-iodo-methane | 2.54 | 100 | a |
| Di-iodo-methane | 1.27 | 100 | a |
| 1-iodo-ethane | 1.27 | 100 | a |
| 1-iodo-ethane | 2.54 | 0 | b |
| Methyl iodide | 0.42 | 0 | b |
| Methyl iodide | 1.27 | 0 | b |

EXAMPLE 7

This trial was a comparison of methyl iodide, diiodomethane and 1-iodoethane at 0.42, 0.84, 1.27, 1.69, and 2.11 μM/ml (equal to ¼, ½, ¾, 1 and 1¼ lb methyl bromide/100 ft$^3$). Phytophthora parasitica was used as the test organism. Soil moisture was 32% with a fumigation time period of 48 hours. There were 4 replications per treatment. Methyl iodide applications at all concentrations were the best treatments and were significantly different from all other treatments. This was followed by diiodomethane and 1-iodoethane at 2.11 and diiodomethane at 1.69 and 1.27 μM/ml. All other treatments were not significantly different from the control.

TABLE 6

| Chemical | μM/ml MI | % survival | Note |
|---|---|---|---|
| None | 0 | 100 | a |
| Di-iodo-methane | 0.42 | 100 | a |
| Di-iodo-methane | 0.84 | 100 | a |
| 1-iodo-ethane | 0.42 | 100 | a |
| 1-iodo-ethane | 0.84 | 100 | a |
| 1-iodo-ethane | 1.27 | 100 | a |
| 1-iodo-ethane | 1.69 | 100 | a |
| Di-iodo-methane | 1.27 | 87 | b |
| Di-iodo-methane | 1.69 | 78 | bc |
| 1-iodo-ethane | 2.11 | 70 | c |
| Di-iodo-methane | 2.11 | 66 | c |
| Methyl iodide | 0.42 | 0 | d |
| Methyl iodide | 0.84 | 0 | d |
| Methyl iodide | 1.27 | 0 | d |
| Methyl iodide | 1.69 | 0 | d |
| Methyl iodide | 2.11 | 0 | d |

EXAMPLE 8

The test soil for this field trial was a sandy loam averaging 5.85% moisture at 15 cm. The trial was a randomized block with 7 treatments of 4 replications each. The test organism was *Phytophthora parasitica* prepared as described above and incubated on the laboratory bench overnight before placement in the field. Fumigants used were methyl bromide at 454, 227 and 113.5 g/9 m$^2$ (1, ½ and ¼ lb/100 ft$^2$) and methyl iodide at 684, 342 and 171 g/9 m$^2$ (1.5, 0.75 and 0.325 lb/100 ft$^2$). These rates are 4.8, 2.4 and 1.2 moles.

Methyl iodide and methyl bromide were similar in performance. There were low percentages of recovery in six fumigated plots. At 2.4 M both MI and MBr had two plots with recovered organisms. MI had a 1 percent recovery at 4.8 M and MBr had a 1 percent at 1.2 M. The highest rate of recovery for MBr was 3% at 2.4 M and a 12 inch depth, while for MI it was 4% at 2.4 M at 6 inches. All controls were recovered at 100% (Table 7).

TABLE 7

(field trial 1)

| Chemical | M/100 ft$^3$ | depth (in) | % recovery | Note |
|---|---|---|---|---|
| Control | 0 | 1 | 100 | a |
| Control | 0 | 6 | 100 | a |
| Control | 0 | 12 | 100 | a |
| MI | 2.4 | 6 | 4 | b |
| MBr | 2.4 | 12 | 3 | bc |
| MI | 2.4 | 1 | 2 | bc |
| MBr | 2.4 | 6 | 1 | bc |
| MI | 4.8 | 6 | 1 | bc |
| MI | 1.2 | 12 | 1 | bc |
| MBr | 1.2 | 1 | 0 | c |
| MBr | 1.2 | 6 | 0 | c |
| MBr | 1.2 | 12 | 0 | c |
| MBr | 2.4 | 1 | 0 | c |
| MBr | 4.8 | 12 | 0 | c |
| MI | 1.2 | 1 | 0 | c |
| MI | 1.2 | 6 | 0 | c |
| MI | 2.4 | 12 | 0 | c |
| MI | 4.8 | 1 | 0 | c |
| MI | 4.8 | 12 | 0 | c |
| MBr | 4.8 | 1 | 0 | c |
| MBr | 4.8 | 6 | 0 | c |

EXAMPLE 9

In this field trial, soil moisture averaged 9.5% between 15 and 30 cm. Methyl bromide was applied as in Example 8. Methyl iodide was mixed with 95% ethanol and poured in a cross pattern across the plot for better distribution. Fumigant rates were as in Example 5. The ethanol was mixed at 160, 80 and 40 ml for the high, medium and low rates, respectively. Controls were non-treated and ethanol at 160 ml/plot. Plots were fumigated for 4 days and aerated 1 day before plating.

MI and MBr were again similar in performance, although the percent recovery in fumigated plots ranged from 24 to 45% at rates of 1.2 M for 4 plots (2 MI and 2 MBr) and 2.4 M for one plot (MBr). Controls at 6 and 12 inch depths were recovered at 99 to 100%. All treatments at 1 inch depth had 0% recovery due to the effects of solarization (Table 8).

TABLE 8

(field trial 2)

| Chemical | M/100 ft$^3$ | depth (in) | % recovery | Note |
|---|---|---|---|---|
| Control | 0 | 6 | 100 | a |
| Control | 0 | 12 | 99 | a |
| Ethanol | 0 | 6 | 99 | a |
| Ethanol | 0 | 12 | 99 | a |
| MI | 1.2 | 12 | 45 | b |
| MBr | 2.4 | 12 | 25 | bc |
| MBr | 1.2 | 6 | 25 | bc |
| MBr | 1.2 | 12 | 25 | bc |
| MI | 1.2 | 6 | 24 | bc |
| MBr | 1.2 | 1 | 0 | c |
| MBr | 2.4 | 1 | 0 | c |
| MBr | 2.4 | 6 | 0 | c |
| MBr | 4.8 | 1 | 0 | c |
| MBr | 4.8 | 6 | 0 | c |
| MBr | 4.8 | 12 | 0 | c |
| MI | 1.2 | 1 | 0 | c |
| MI | 2.4 | 1 | 0 | c |
| MI | 2.4 | 6 | 0 | c |
| MI | 2.4 | 12 | 0 | c |
| MI | 4.8 | 1 | 0 | c |
| MI | 4.8 | 6 | 0 | c |
| MI | 4.8 | 12 | 0 | c |
| Control | 0 | 1 | 0 | c |
| Ethanol | 0 | 1 | 0 | c |

EXAMPLE 10

The effects of MI fumigation on three weed seeds were determined. The percent survival of these seed after fumigation with different concentrations of MI is reported in Table 9. The percent survival is calculated by dividing the number of treated germinated seeds by the number of untreated germinated seeds.

| Treatment | Weed Species | | |
|---|---|---|---|
| μM/ml MI | Annual Bluegrass | Cheeseweed | Field Bindweed |
| 1.69 | 0 | 0 | 3.6 |
| 1.27 | 0 | 0 | 1.8 |
| 0.84 | 0 | 0 | 0 |
| 0.42 | 0 | 0 | 1.8 |
| 0.21 | 0 | 0 | 5.4 |

EXAMPLE 11

The effects of MI treatment on the nematode *Meloidogyne incognita* were determined. The percent survival after fumigation at different concentrations of MI are reported in Table 10. The percent survival was calculated by dividing the number of treated surviving nematodes by the number of untreated surviving nematodes.

| μM/ml MI | percent survival |
| --- | --- |
| 0.052 | 0 |
| 0.026 | 0 |
| 0.013 | 0 |
| 0.006 | 55 |
| 0.003 | 65 |

EXAMPLE 12

The effects of MI on the citrus nematode *Tylenchulus semipenetrans* were determined, The numbers surviving after fumigation at different concentrations of MI are reported in Table 11,

| Rate (lb/ac - μM/container) | Mean | Fisher's protected LSD p = .05 |
| --- | --- | --- |
| 25 lb/ac (0.95 μM) | 0.000 | a |
| 15 lb/ac (0.57 μM) | 0.250 | a |
| 5 lb/ac (0.19 μM) | 4.000 | a |
| 2 lb/ac (.072 μM) | 64.750 | b |
| 0 lb/ac (0 μM) | 223.000 | c |

EXAMPLE 13

The effects of methyl iodide, methyl bromide, clear and black plastic covers on survival of weeds in the soil were examined.

| Platic[1] | No Treatment | Methyl Bromide[2] | Methyl Iodide |
| --- | --- | --- | --- |
| None | 2[3] | Not used | Not used |
| Clear | 1.5 | 4.75 | 5 |
| Black | 2.25 | 4.75 | 4.5 |

[1] 4 mil thick.
[2] Methyl bromide and methyl iodide were used at 4.8 M/100 ft$^2$.
[3] Rating 1–5: 1 = dense weed population; 5 = no weeds.

While the present invention has been described with reference to preferred embodiments and illustrative examples, it should be understood that one of ordinary skill in the art after reading the foregoing specification would be able to effect various changes, substitutions of equivalents and modifications to the methods as described herein. Therefore, it is intended that the scope of the invention not be limited by reference to the illustrative examples, but rather with reference to the accompanying claims.

What is claimed is:

1. A method for soil fumigation, comprising:

applying to soil a fumigatingly effective amount of methyl iodide.

2. A method according to claim 1, wherein the effective amount is between about 2 lb/acre and about 2000 lb/acre.

3. A method according to claim 2, wherein the effective amount is between about 500 lb/acre and about 1500 lb/acre.

4. A method according to claim 3, wherein the effective amount is between about 600 lb/acre and about 1200 lb/acre.

5. A method according to claim 1, wherein methyl iodide is applied in combination with at least one additional fumigant.

6. A method according to claim 5, wherein the additional fumigant is carbon disulfide or chloropicrin.

7. A method according to claim 1, wherein the methyl iodide is preheated prior to application.

8. A method according to claim 1, wherein the soil is tarped following application.

9. A method according to claim 1, wherein the methyl iodide is dissolved in a suitable solvent.

10. A method according to claim 9, wherein the solvent is selected from the group consisting of alcohols, acetone, and mixtures of water and alcohol or acetone.

\* \* \* \* \*

UNITED STATES PATENT AND TRADEMARK OFFICE
CERTIFICATE OF CORRECTION

PATENT NO. : 5,518,692

DATED : May 21, 1996

INVENTOR(S) : Nigel M. Grech, Howard D. Ohr and James J. Sims

It is certified that error appears in the above-indentified patent and that said Letters Patent is hereby corrected as shown below:

| COLUMN | LINE | |
|---|---|---|
| 1 | 23 | Change "Fusadum" to --Fusarium-- |
| 1 | 26 | Change "Paratdchodorus" to --Paratrichodorus-- |
| 1 | 27 | Change "Dilylenchus" to --Ditylenchus-- |
| 3 | 14 | Change "Hassail" to --Hassall-- |
| 3 | 60 | Change "Was" to --was-- |
| 4 | 48 | Change "fiat" to --flat-- |
| 5 | 38 | Change "Paratrichodonts" to --Paratrichodorus-- |
| 5 | 46 | Change "Convolvuhts" to --Convolvulus-- |
| 7 | 33 | Change "solanis" to --solani-- |
| 9 | 23 | Change "0.42/IM/ml" to --0.42 $\mu$M/ml-- |
| 11 | 51 | Change "1.-iodobutane" to --1-iodobutane-- |
| 11 | 56 | Change "Organism" to --organism-- |
| 11 | 63 | Change "=to" to --= to-- |

UNITED STATES PATENT AND TRADEMARK OFFICE
CERTIFICATE OF CORRECTION

PATENT NO. : 5,518,692
DATED : May 21, 1996
INVENTOR(S) : Nigel M. Grech, Howard D. Ohr and James J. Sims

It is certified that error appears in the above-indentified patent and that said Letters Patent is hereby corrected as shown below:

| COLUMN | LINE | |
|---|---|---|
| 12 | 31 | Change "$\mu$M/ml=to" to --$\mu$M/ml to-- |
| 15 | 13 | Change "," to --.-- |
| 15 | 15 | Change "," to --.-- |
| 15 | 18 | Change "p = .05" to --p=.05-- |
| 15 | 33 | Change "Platic[1]" to --Plastic[1]-- |

Signed and Sealed this

Twenty-fourth Day of December, 1996

Attest:

BRUCE LEHMAN

*Attesting Officer*     *Commissioner of Patents and Trademarks*